(12) United States Patent
Levitan

(10) Patent No.: US 9,452,273 B2
(45) Date of Patent: Sep. 27, 2016

(54) SURGICAL DEVICE FOR CRICOTHYROTOMY AND THE LIKE

(71) Applicant: Richard M. Levitan, Radnor, PA (US)

(72) Inventor: Richard M. Levitan, Radnor, PA (US)

( * ) Notice: Subject to any disclaimer, the term of this patent is extended or adjusted under 35 U.S.C. 154(b) by 312 days.

(21) Appl. No.: 13/834,429

(22) Filed: Mar. 15, 2013

(65) Prior Publication Data

US 2014/0148837 A1    May 29, 2014

Related U.S. Application Data

(60) Provisional application No. 61/730,643, filed on Nov. 28, 2012.

(51) Int. Cl.
*A61M 16/04* (2006.01)
*A61B 17/3211* (2006.01)
*A61B 17/02* (2006.01)
*A61B 17/3209* (2006.01)

(52) U.S. Cl.
CPC ....... *A61M 16/0472* (2013.01); *A61B 17/3211* (2013.01); *A61B 17/02* (2013.01); *A61B 17/32093* (2013.01); *A61B 2017/32113* (2013.01)

(58) Field of Classification Search
CPC ............. A61B 17/3209; A61B 17/32093; A61B 17/3211; A61B 2017/32113; A61M 16/0472
See application file for complete search history.

(56) References Cited

U.S. PATENT DOCUMENTS

| | | |
|---|---|---|
| 338,612 A | 3/1886 | Pusey |
| 5,988,168 A | 11/1999 | Bair |
| 6,402,770 B1 | 6/2002 | Jessen |
| 6,915,804 B2 | 7/2005 | Melker et al. |
| 7,308,896 B2 | 12/2007 | Cruz |
| D589,145 S | 3/2009 | Miller |
| 7,540,875 B2 | 6/2009 | Jessen |
| 2005/0101983 A1* | 5/2005 | Loshakove .... A61B 17/320016 606/185 |
| 2005/0279363 A1 | 12/2005 | Cruz |
| 2008/0257359 A1 | 10/2008 | Rumsey |

(Continued)

FOREIGN PATENT DOCUMENTS

| | | |
|---|---|---|
| WO | WO2009102941 A1 | 8/2009 |
| WO | WO2009146149 A2 | 12/2009 |

OTHER PUBLICATIONS

"CRIC Cricothyroidotomy Kit Trainer's Manual", Jul. 2011, Retrieved from http://www.pyng.com/education/training-manuals-2/?pi=152.

Walsh, R., et al., "Emergency Physician Evaluation of a Novel Surgical Cricothyroidotomy Tool in Simulated Combat and Clinical Environments", Military Medicine, vol. 178, No. 1, pp. 29-33.

(Continued)

*Primary Examiner* — Todd J Scherbel
(74) *Attorney, Agent, or Firm* — Mendelsohn Dunleavy, P.C.; Steve Mendelsohn

(57) ABSTRACT

For cricothyrotomy and the like, a surgical device has, in one embodiment, a device body with a bi-directional scalpel, an end cap, and a tracheal hook that fits within a channel formed in the device body. With the end cap removed to expose the bi-directional scalpel blade and with the tracheal hook fully inserted within the body channel, the device can be held, e.g., in the dominant hand of an operator, and manipulated to make an opening in the patient's neck using the exposed scalpel blade. The tracheal hook can then be slid away from the device body with the hook's barbed tip entering the opening to enable the operator to easily and quickly secure the surgical airway. The design of the surgical device enables an economy of movements that otherwise would typically not be within the skill set of an operator who was not a surgeon.

20 Claims, 9 Drawing Sheets

(56) References Cited

U.S. PATENT DOCUMENTS

2010/0089405 A1    4/2010  Johnson et al.
2011/0270292 A1*  11/2011  Saito .............................. 606/167
2012/0130417 A1*  5/2012  Lepulu ............... A61B 17/3478
                                                                       606/198

OTHER PUBLICATIONS

European Search Report; Mailed Feb. 24, 2014 for corresponding EP Application No. 13005092.5.

* cited by examiner

100

FIG. 2
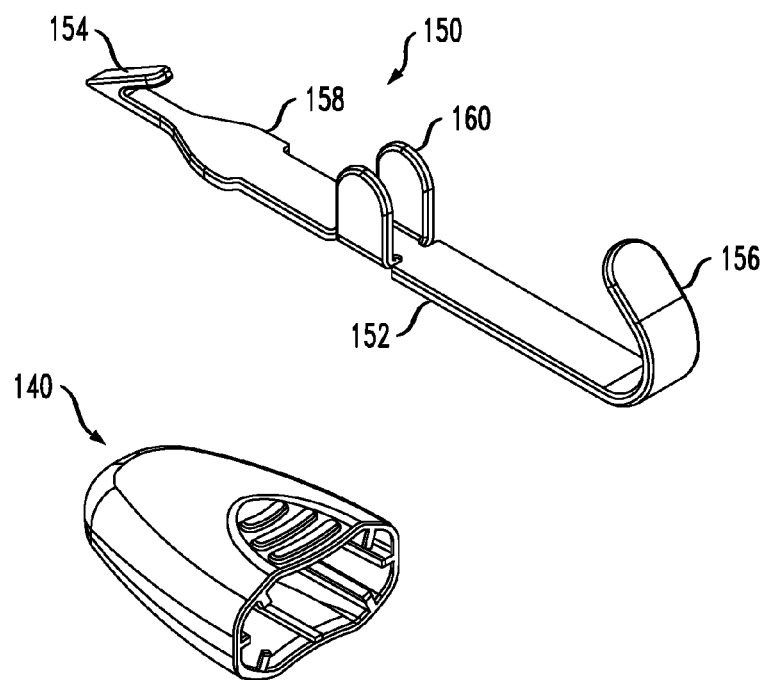
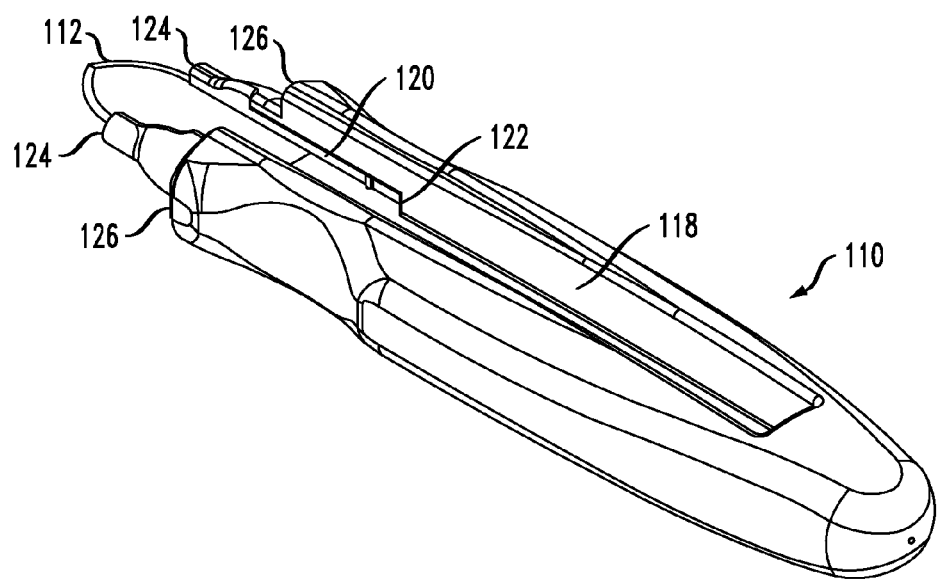

FIG. 3
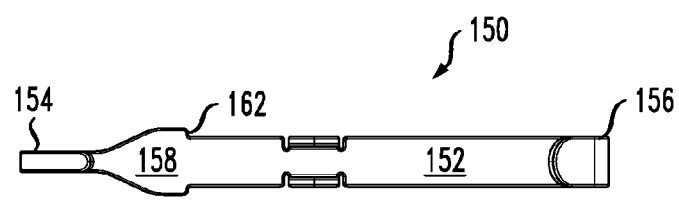
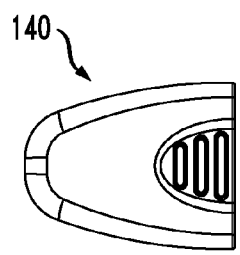
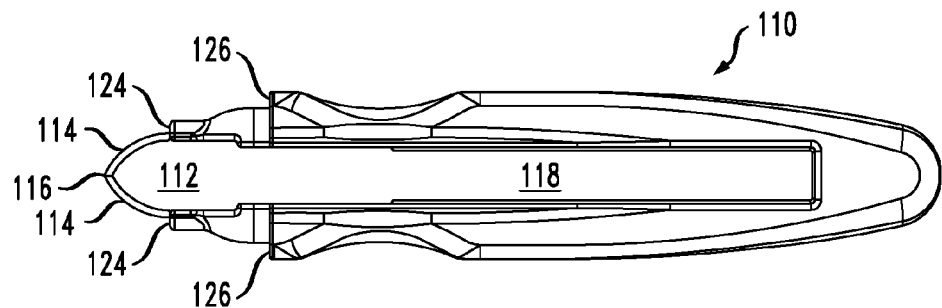

100

100

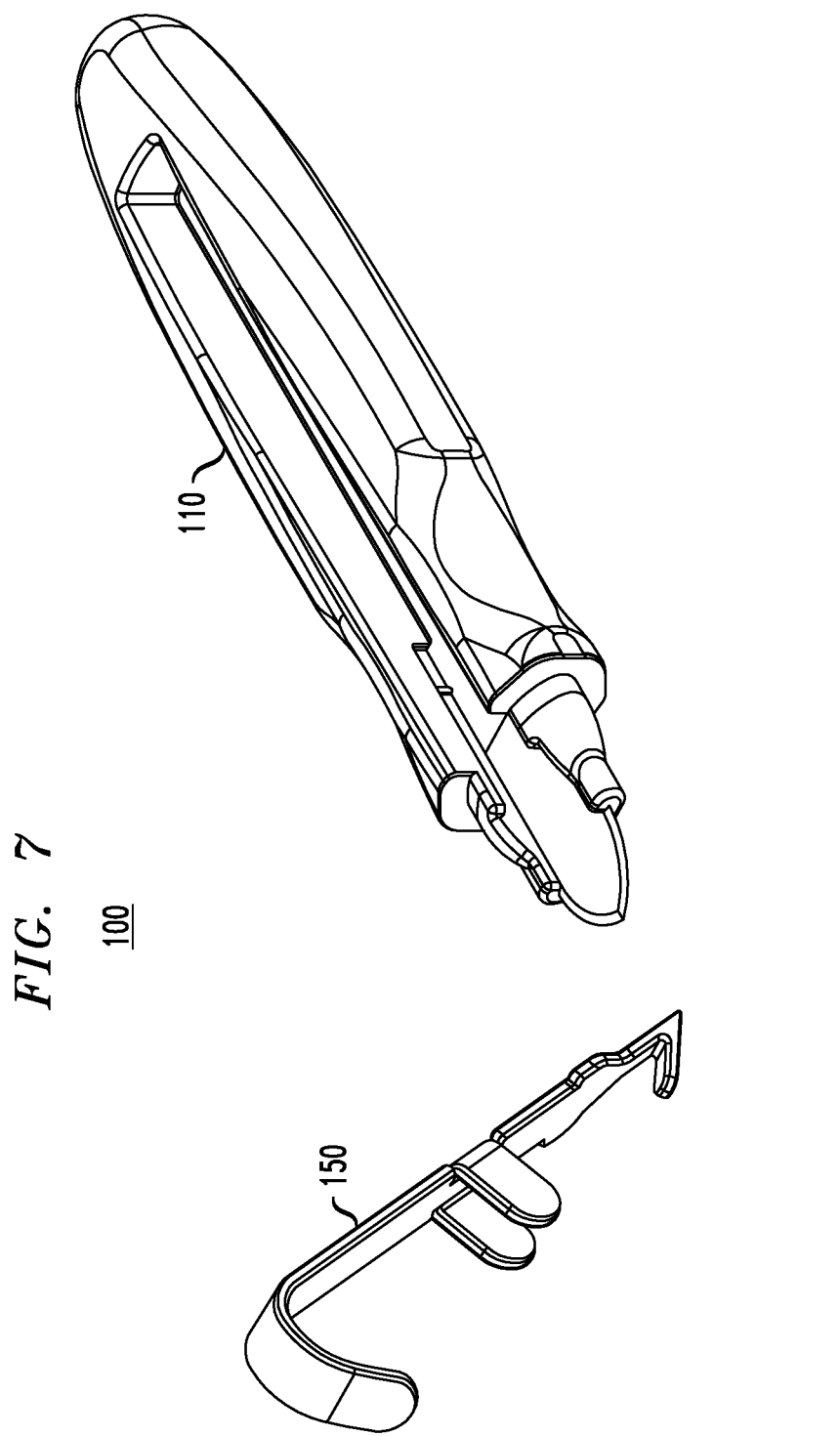

SURGICAL DEVICE FOR CRICOTHYROTOMY AND THE LIKE

CROSS-REFERENCE TO RELATED APPLICATIONS

This application claims the benefit of the filing date of U.S. provisional application No. 61/730,643, filed on Nov. 28, 2012, the teachings of which are incorporated herein by reference in their entirety.

BACKGROUND

1. Field of the Invention

The present invention relates to surgical airways and, more specifically but not exclusively, to a device for performing cricothyrotomies and the like.

2. Description of the Related Art

This section introduces aspects that may help facilitate a better understanding of the invention. Accordingly, the statements of this section are to be read in this light and are not to be understood as admissions about what is prior art or what is not prior art.

Cricothyrotomy involves the creation of a surgical incision in the space between the cricoid and thyroid cartilages for the placement of a breathing tube. It is done in situations of massive facial injury, and other instances of inability to oxygenate and ventilate through the mouth. The standard approach involves a vertical skin incision, blunt dissection down to the cricothyroid membrane, and then a horizontal incision through the membrane itself. To stabilize the trachea while inserting a breathing tube, many operators use a tracheal hook. This is a sharp pointed hook, which is used to lift the inferior aspect of the thyroid during tube insertion.

The mechanics of handling the scalpel, making both vertical and horizontal incisions, and then placing the hook in the right position can be challenging. The horizontal incision often needs to be made in two directions to create a wide enough hole. Since standard scalpels cut in only one direction, the instrument must be rotated 180 degrees to be able to cut in both directions. Furthermore, over-insertion of the scalpel blade tip can injure the trachea, and excessive lateral movement of the scalpel can injure the great vessels of the neck. Because of the technical challenges of the procedure, and the extreme clinical situations in which it is often required, there is a high rate of failure. In the battlefields of Iraq and Afghanistan, for example, one third of surgical airways were unsuccessful.

BRIEF DESCRIPTION OF THE DRAWINGS

Other embodiments of the invention will become more fully apparent from the following detailed description, the appended claims, and the accompanying drawings in which like reference numerals identify similar or identical elements.

FIG. 2 shows an exploded perspective view of the surgical device of FIG. 1;

FIG. 3 shows an exploded plan view of the surgical device of FIG. 1;

FIG. 7 shows a perspective view of the surgical device of FIG. 1 with the cap removed and the tracheal hook fully disengaged from and pivoted away from the device body;

FIGS. 9(A)-8(D) respectively show perspective, plan, side, and end views of the tracheal hook for the surgical device of FIG. 8.

DETAILED DESCRIPTION

Figure 1:
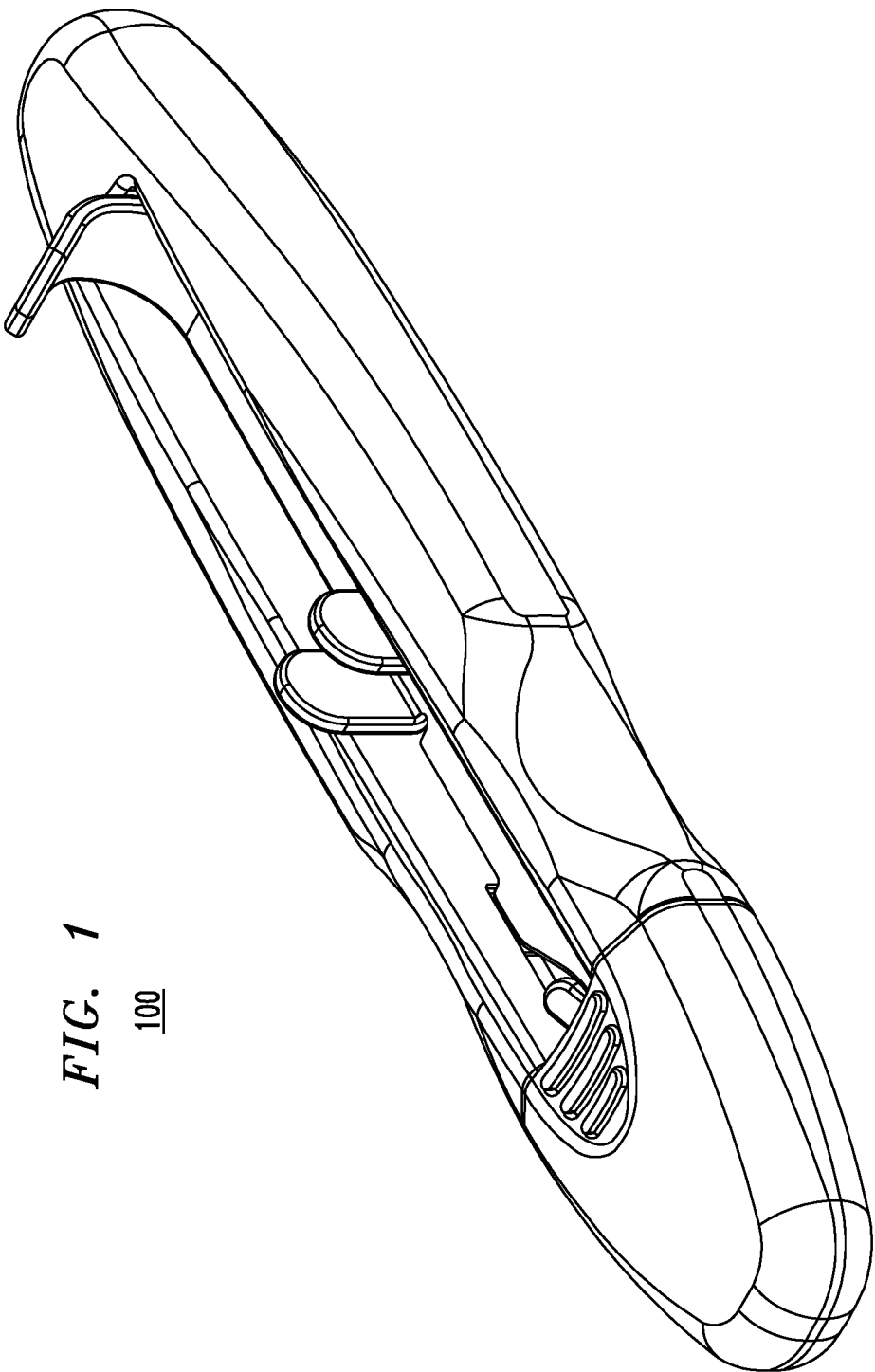
FIG. 1 shows a perspective view of a surgical device for cricothyrotomy, according to one embodiment of the disclosure.

As represented in FIGS. 1-7, surgical device 100 includes a device body 110, an end cap 140, and tracheal hook 150.

Tracheal hook 150 includes a planar intermediate portion 152 with a barbed tip 154 at one end and a curved handle 156 at the other end. Intermediate portion 152 has an intermediate flange 158 near the tip end of the hook and a medial thumb rest 160. The barb of tip 154 and the curve of handle 156 extend towards each other on the same side of intermediate portion 152 having thumb rest 160.

Figure 4:
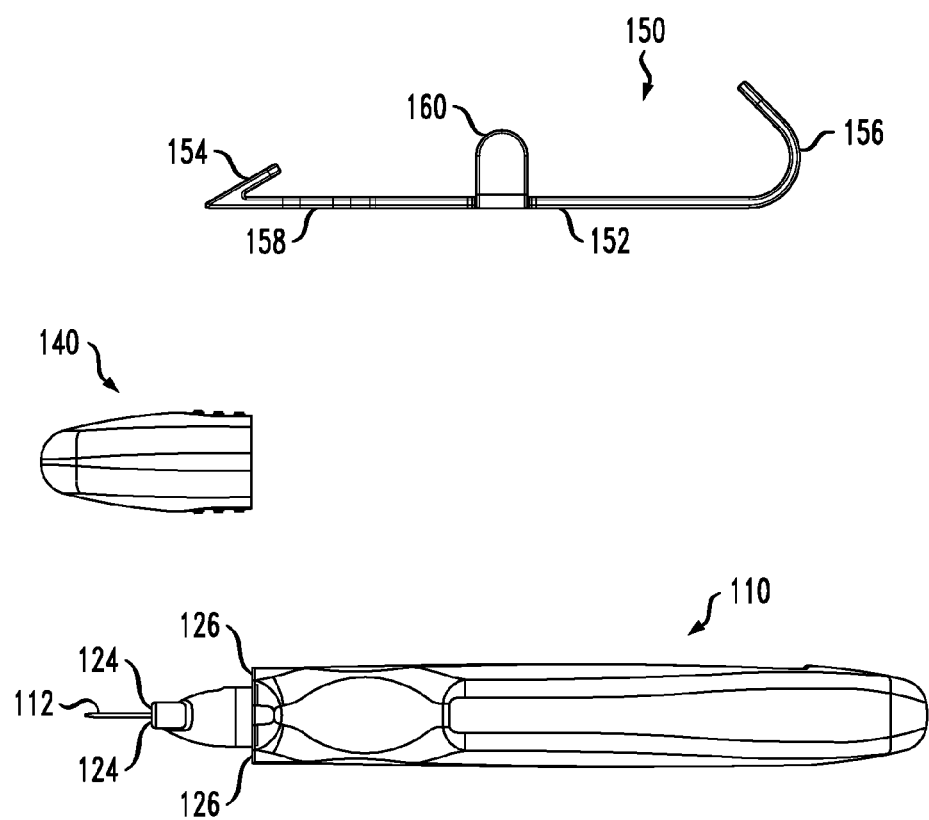
FIG. 4 shows an exploded side view of the surgical device of FIG. 1.

Statically mounted within body 110 is a bidirectional scalpel 112 having a blade with two opposing cutting edges 114 that meet at a cutting point 116 and define the cutting plane of scalpel 112, which cutting plane is coplanar to the plane of FIG. 3 and normal to the plane of FIG. 4. The blade of scalpel 112 extends beyond the end of body 110 by a distance that is approximately equal to the maximal width of that extended portion of scalpel 112 (e.g., about 1 cm).

Formed within body 110 is a channel 118 for receiving hook 150. Formed within channel 118 are two opposing grooves 120 for receiving the two opposing sides of flange 158 of hook 150. Flange 158 has two corners 162 that limit the distance that hook 150 can be slid into body 110 when the two corners 162 abut the proximal ends 122 of the two grooves 120. Although not shown in the figures, hook 150 and/or channel 118 have suitable structure(s) (e.g., small projection(s)) that function(s) as detent(s) to secure hook 150 within body 110 when hook 150 is fully inserted within channel 118, such that the tip of the hook is held in a position within the channel, not projecting over the cutting region of the scalpel.

Underneath the scalpel, on the inferior aspect of the body (just proximal to the blade), the body has an enlargement 124 that functions as a tip-stop limiting over-insertion of the device into the opening. Cap seat 126, which mates with cap 140, provides a further tip-stop. The outside aspect of the distal end of the hook 150 is rounded enough to inhibit injury to the trachea if it contacts the posterior tracheal wall. Along the middle of the hook, which lies within the channel of the body 110, is a series of ridges (not shown) that facilitate advancement of the hook down the channel. The shape of the tracheal hook is designed to slide easily down the channel. When the hook is advanced down the channel, the distal, leading edge of the hook slides flush with the scalpel, and then the hook can be pivoted out of the channel. The hook is deflected upward, out of the channel when the flange 158 slides free of the grooves 120 in the channel.

Cap 140 is used for storage and shipment of the device. It helps protect users from the scalpel and stabilizes the hook within the body channel. The leading edge of the cap can have a small cross-shaped projection that, if desired, can be held against the skin of the patient to create an indentation marking the intended incision site. The cap should also be able to be stored on the back of the body (so that the scalpel can be recapped if needed at the end of the procedure).

Figure 5:
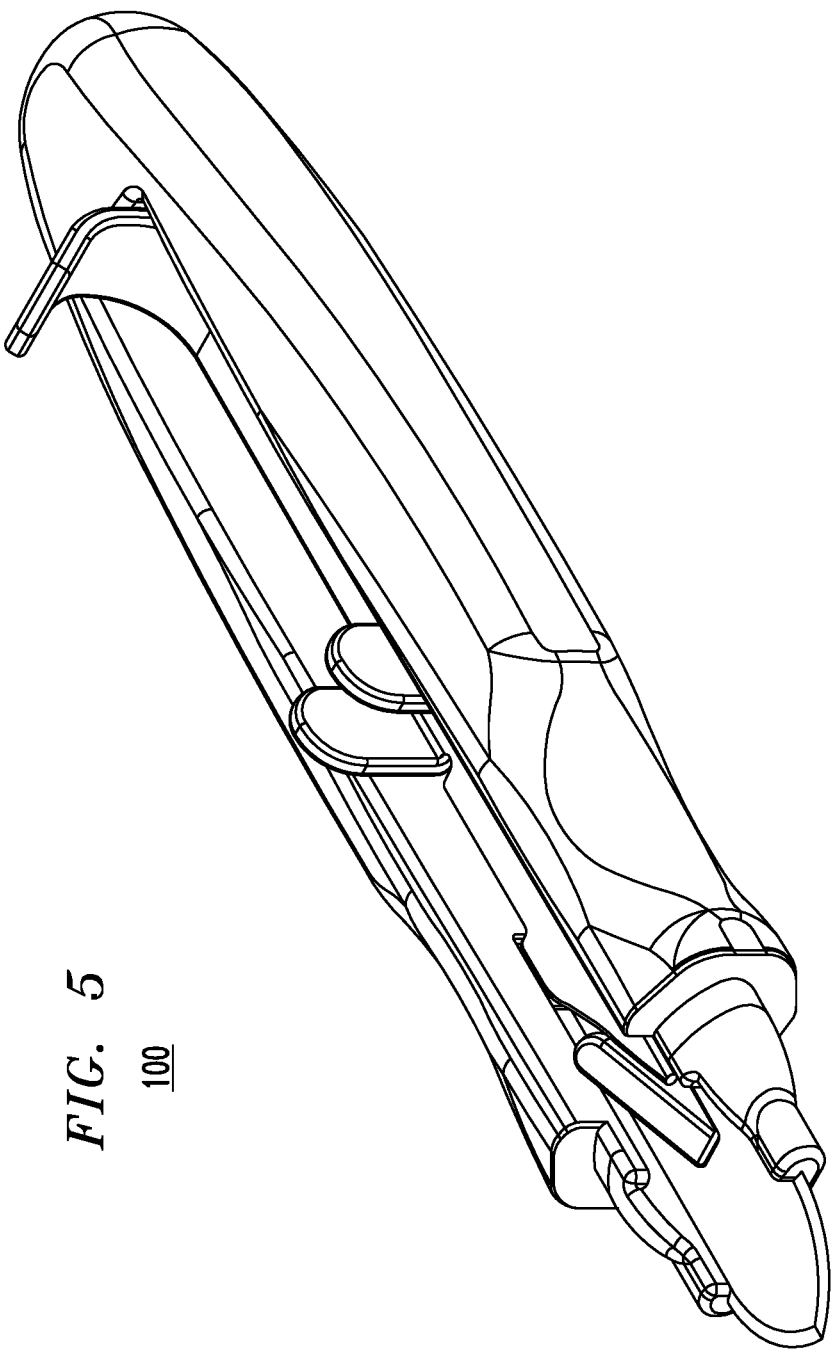
FIG. 5 shows a perspective view of the surgical device of FIG. 1 with the cap removed and the tracheal hook fully engaged within the device body.

To perform a cricothyrotomy or other similar procedure, a person (i.e., the operator) holds the fully assembled device 100 represented in FIG. 1 by the body 110 with his/her dominant hand and removes the cap 140 with his/her non-dominant hand. Continuing to hold the body with his/her dominant hand, the operator then uses the device as represented in FIG. 5 to make an opening at the desired site on the patient (e.g., the patient's neck). In particular, the operator stabs the site with the cutting point 116 of scalpel 112 to make an initial opening and then widens that initial opening using both cutting edges 114 of scalpel 112 by making side-to-side movements of the scalpel within the scalpel's cutting plane while continuing to introduce the scalpel further and further into the opening.

Figure 6:
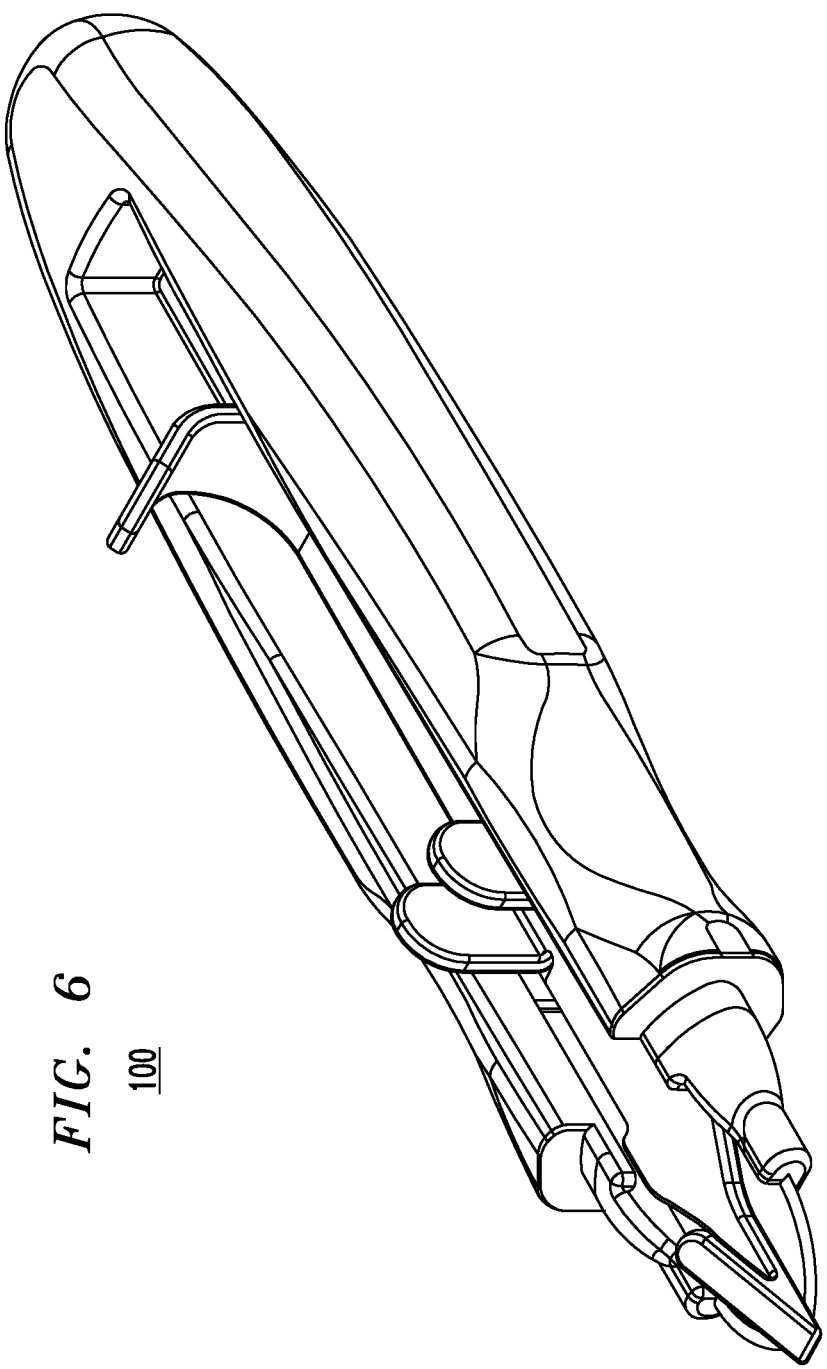
FIG. 6 shows a perspective view of the surgical device of FIG. 1 with the cap removed and the tracheal hook partially disengaged from the device body.
Figure 8A:
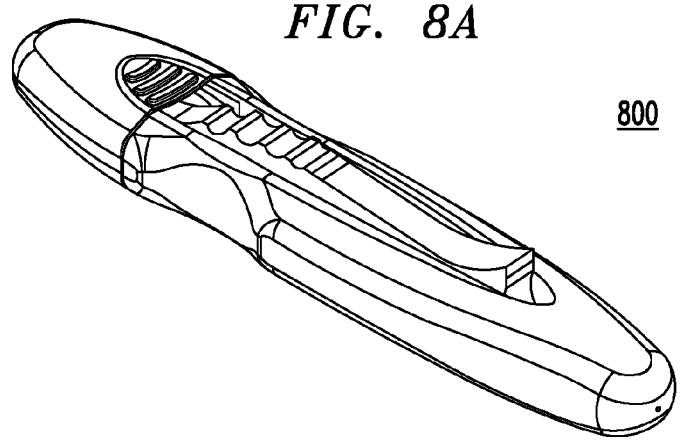
FIGS. 8(A)-8(D) respectively show perspective, plan, side, and end views of a surgical device for cricothyrotomy, according to another embodiment of the disclosure.
Figure 8B:
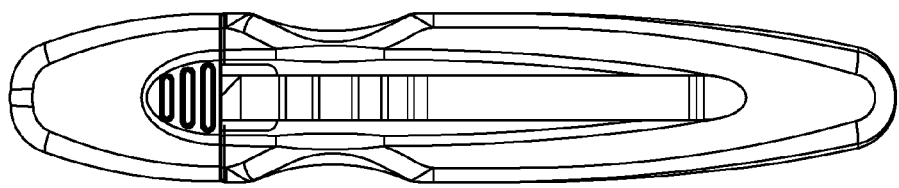
Figure 8C:
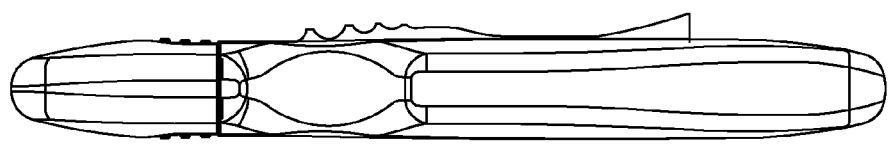
Figure 8D:
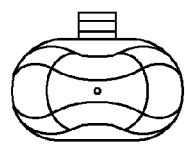
Figure 9A:
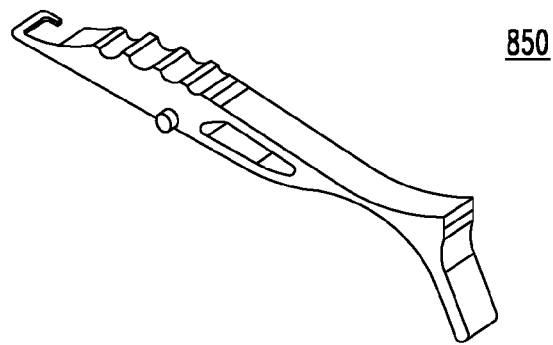
Figure 9B:
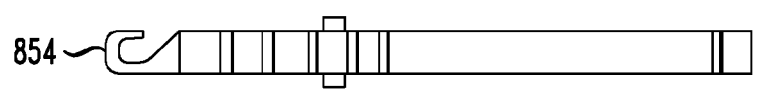
Figure 9C:
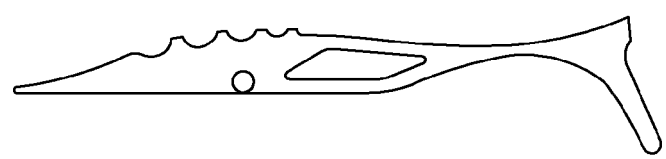
Figure 9D:
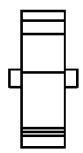

After the opening is sufficiently large and/or after the extended portion of scalpel 112 has been fully inserted into the opening, the operator can push on thumb rest 160 using his/her non-dominant hand or the thumb of his/her dominant hand to begin to slide the hook 150 away from the body 110 such that the barbed tip 154 of the hook enters the opening with the device as represented in FIG. 6. The operator can continue to slide the hook away from the device body until the hook is fully disengaged from the body (i.e., the flange 158 fully disengaged from the grooves 120) as represented in FIG. 7. Note that, as shown in FIG. 7, when the flange is fully disengaged from the grooves, the hook is free to pivot with respect to the device body. At this point, the operator can remove the device body from the site of the opening using one hand while retaining the hook 150 (with the other hand) with its barbed tip within the opening in the patient. The opening can be enlarged if needed by reinsertion of the scalpel, or a tube or introducer can be inserted into the opening. Some devices and techniques that could be used are described in U.S. patent application Ser. No. 13/501,602 and U.S. patent application Ser. No. 13/484,933, the teachings of both of which are incorporated herein by reference.

In one possible implementation of the device, the device body is ovoid in cross-sectional shape, with a length between 4 and 6 inches. The body is shaped to provide an easy grip. The base of the scalpel lies flush with the bottom of body channel, so there is a smooth transition from the channel to the blade. The blade tip has a chevron, triangular, or slightly rounded triangular shape. This allows cutting in either direction. The blade size and shape are designed to cut the skin, and to penetrate the cricothyroid membrane, but also to prevent over-insertion. The scalpel tip size, e.g., a length and width of approximately 1 centimeter each, is intended to be smaller than the average trachea diameter, which is typically between 14-18 mm for females and 15-21 mm for males. Conversely, the incision created by the scalpel should also be large enough for insertion of a small tracheotomy or tracheal tube, which have external diameters from about 6 mm to about 10 mm.

The device body may be gripped like a pen, in the dominant hand. The non-dominant hand may be used to palpate the thyroid and other laryngeal landmarks. The non-dominant hand may be kept on the thyroid cartilage throughout the procedure, pinched between the first and third fingers. After the dominant hand (gripping the body) makes a vertical incision through the skin, the index finger of the non-dominant hand may bluntly dissect the tissue to get down to the cricothyroid membrane. The operator may then rotate the direction of the blade tip and plunge the scalpel tip through the cricothyroid membrane. With a small side-to-side movement, the scalpel may be used to widen the horizontal incision through the membrane.

With the scalpel tip inside the trachea, the tracheal hook can be slid down the channel, dropping the hook tip into trachea. The advancement can be done either with the thumb or fingers of the dominant hand that is gripping the body, or with a finger or thumb of the non-dominant hand.

As the hook is advanced down the channel, the hook pivots out of the channel, away from the body. This allows gripping of the hook with the dominant or non-dominant hand, manipulating the barbed tip of the hook into a position that permits upward traction on the inferior aspect of the thyroid. The design of the tracheal hook sliding within the channel, and the shape and alignment of the hook tip with the scalpel blade tip, are intended to yield a smooth transition from the horizontal incision (of an appropriate size) to stabilization of the trachea (with the hook).

Once the opening in the membrane has been made and the hook is in place, the dominant or non-dominant hand can put down the device body, and then pick up a breathing tube or tube-introducer and place it into the trachea. Once the tube is inserted, the tracheal hook is removed and the tube secured.

FIG. 8 represents a surgical device 800 for cricothyrotomy, according to another embodiment of the disclosure. FIG. 9 represents the tracheal hook 850 for surgical device 800. As shown, for example, in FIGS. 2 and 4, in surgical device 100, barbed tip 154 of tracheal hook 150 extends out of the plane defined by intermediate portion 152 on the same side as handle 156. In surgical device 800, on the other hand, the barbed tip 854 of tracheal hook 850 lies within the analogous plane of the device. This orientation of the barbed tip may make easier the insertion of the tracheal hook into an opening in the patient's neck.

Certain embodiments may provide one or more of the following advantages:
(1) The device coordinates into a smooth mechanism the incision through the membrane and placement of the hook into the trachea. This is especially valuable to non-surgically trained airway managers, such as combat medics or other emergency personnel.
(2) The storage of the hook within the body channel prevents loose instruments in the surgical field, an important consideration in environments such as the emergency department, pre-hospital, or battlefield.
(3) The scalpel shape permits vertical and horizontal incisions, and when placed into the cricothyroid membrane, does not require flipping of the scalpel because of its bidirectional cutting edge. Its shape and dimensions limit the risk to the posterior trachea or an over-aggressive lateral incision.
(4) Any operator familiar with a hook and scalpel will recognize the intended use of the instrument. Conversely, the hook and body can be separated and used in a manner similar to the way two separate instruments would be used. In time sensitive, critical clinical care situations, a self-evident mechanism of use is essential.
(5) The overall shape and size of the device yields a small and secure package, another advantage for use in combat or tactical medicine settings.
(6) The device can be effectively used by either a right-hand or left-hand dominant operator.

The scalpel may be made of stainless steel or other material typically used for surgical scalpel blades. The hook may be made of stainless steel or other material typically used for tracheal hooks. The body may be molded or injected or otherwise formed from a suitable plastic material.

Unless explicitly stated otherwise, each numerical value and range should be interpreted as being approximate as if the word "about" or "approximately" preceded the value of the value or range.

It will be further understood that various changes in the details, materials, and arrangements of the parts which have been described and illustrated in order to explain embodiments of this invention may be made by those skilled in the art without departing from embodiments of the invention encompassed by the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. A surgical device comprising:
   a device body;
   a tracheal hook; and
   a planar scalpel mounted to extend beyond a first end of the device body and defining a cutting plane extending parallel to the planar scalpel, wherein:
   the device body of the surgical device has a channel configured to slidably and removably receive the tracheal hook at the first end of the device body of the surgical device;
   the tracheal hook of the surgical device has, at a first end, a barbed tip having a planar barb that extends away from the cutting plane of the scalpel from a first end of the planar barb to a second end of the planar barb along a plane, the first end of the planar barb coupled to a planar portion of the tracheal hook at the first end of the tracheal hook, the second end of the planar barb defining a free end of the planar barb;
   the planar portion of the tracheal hook defining a plane which is constrained to be parallel to the cutting plane; and
   the planar barb (a) forms an acute angle with the planar portion of the tracheal hook and (b) extends (1) out of the plane defined by the planar portion of the tracheal hook and (2) back towards a second end of the tracheal hook.

2. The surgical device of claim 1, wherein:
   the tracheal hook is configured to slide along the channel away from the device body into an opening in a patient created using the scalpel; and
   the channel prevents the tracheal hook from rotating about a longitudinal axis of the device body.

3. The surgical device of claim 2, wherein the channel has at least one groove configured to slidably engage a flange of the tracheal hook.

4. The surgical device of claim 2, wherein the tracheal hook is configured to slide completely out of the channel at the first end of the device body, thereby completely removing the tracheal hook from the device body.

5. The surgical device of claim 2, wherein at least one of the tracheal hook and the device body has a detent structure configured to inhibit the tracheal hook from sliding along the channel when the tracheal hook is fully inserted within the channel.

6. The surgical device of claim 2, wherein the barbed tip is configured to enter the opening in the patient as the tracheal hook is slid along the channel away from the device body.

7. The surgical device of claim 1, wherein the scalpel is rigidly mounted within the device body.

8. The surgical device of claim 1, wherein the second end of the tracheal hook has a curved handle.

9. The surgical device of claim 1, wherein the tracheal hook has an intermediate thumb rest.

10. The surgical device of claim 1, wherein the scalpel has a bidirectional blade having two opposing cutting edges.

11. The surgical device of claim 10, wherein the scalpel extends beyond the first end of the device body by a distance substantially equal to a maximum width of an exposed portion of the scalpel.

12. The surgical device of claim 11, wherein the distance is approximately 1 cm.

13. The surgical device of claim 1, further comprising a removable end cap configured to mate to the first end of the device body to enclose the scalpel and inhibit the tracheal hook from sliding out of the channel.

14. The surgical device of claim 1, wherein the device body has one or more enlargements that function as tip-stops configured to inhibit over-insertion of the scalpel into an opening formed in a patient using the scalpel.

15. The surgical device of claim 1, further comprising:
   a removable end cap configured to mate to the first end of the device body to enclose the scalpel and inhibit the tracheal hook from sliding out of the channel, wherein:
   the tracheal hook is configured to slide along the channel away from the device body into an opening in a patient created using the scalpel;
   the channel prevents the tracheal hook from rotating about a longitudinal axis of the device body;
   the channel has opposing grooves configured to slidably engage a flange of the tracheal hook;

the tracheal hook is configured to slide completely out of the channel at the first end of the device body, thereby completely removing the tracheal hook from the device body;

at least one of the tracheal hook and the device body has a detent structure configured to inhibit the tracheal hook from sliding along the channel when the tracheal hook is fully inserted within the channel;

the barbed tip is configured to enter the opening in the patient as the tracheal hook is slid along the channel away from the device body;

the planar barb is rigidly connected to the planar portion of the tracheal hook to form the acute angle;

the scalpel is rigidly mounted within the device body;

the second end of the tracheal hook has a curved handle;

the tracheal hook has an intermediate thumb rest;

the scalpel has a bidirectional blade having two opposing cutting edges;

the scalpel extends beyond the first end of the device body by a distance substantially equal to a maximum width of an exposed portion of the scalpel; and the device body has one or more enlargements that function as tip-stops configured to inhibit over-insertion of the scalpel into the opening in the patient.

16. The surgical device of claim 15, wherein:
the planar barb is rigidly connected to the planar portion of the tracheal hook to form the acute angle;

the surgical device is configured such that the barbed tip of the tracheal hook is in physical contact with the scalpel as the tracheal hook is advanced down the channel towards a blade end of the scalpel; and the barbed tip of the tracheal hook has a straight leading edge that is parallel to the cutting plane of the scalpel.

17. The surgical device of claim 1, wherein the planar barb is rigidly connected to the planar portion of the tracheal hook to form the acute angle.

18. The surgical device of claim 1, wherein the surgical device is configured such that the barbed tip of the tracheal hook is in physical contact with the scalpel as the tracheal hook is advanced down the channel towards a blade end of the scalpel.

19. The surgical device of claim 1, wherein the barbed tip of the tracheal hook has a straight leading edge that is parallel to the cutting plane of the scalpel.

20. The surgical device of claim 1, wherein:
the planar barb is rigidly connected to the planar portion of the tracheal hook to form the acute angle;

the surgical device is configured such that the barbed tip of the tracheal hook is in physical contact with the scalpel as the tracheal hook is advanced down the channel towards a blade end of the scalpel; and the barbed tip of the tracheal hook has a straight leading edge that is parallel to the cutting plane of the scalpel.

* * * * *